US009750527B2

(12) United States Patent
Kostrzewski (10) Patent No.: US 9,750,527 B2
(45) Date of Patent: *Sep. 5, 2017

(54) SURGICAL STAPLING APPARATUS WITH CURVED CARTRIDGE AND ANVIL ASSEMBLIES

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 453 days.

This patent is subject to a terminal disclaimer.

(21) Appl. No.: 14/561,744

(22) Filed: Dec. 5, 2014

(65) Prior Publication Data

US 2015/0083784 A1    Mar. 26, 2015

Related U.S. Application Data

(63) Continuation of application No. 14/180,752, filed on Feb. 14, 2014, now Pat. No. 8,925,787, which is a
(Continued)

(51) Int. Cl.
*A61B 17/04* (2006.01)
*A61B 17/10* (2006.01)
(Continued)

(52) U.S. Cl.
CPC ........ *A61B 17/3209* (2013.01); *A61B 17/068* (2013.01); *A61B 17/072* (2013.01);
(Continued)

(58) Field of Classification Search
CPC .......... A61B 17/072; A61B 2017/2923; A61B 2017/320052; A61B 2019/4857;
(Continued)

(56) References Cited

U.S. PATENT DOCUMENTS

| 3,269,630 A | 8/1966 | Fleischer |
| 3,315,863 A | 4/1967 | O'Dea |

(Continued)

FOREIGN PATENT DOCUMENTS

| EP | 1550412 A2 | 7/2005 |
| EP | 1943965 A2 | 7/2008 |

(Continued)

OTHER PUBLICATIONS

European Office Action corresponding to counterpart Int'l Application No. EP 10 250 334.9 dated Nov. 23, 2015; (4 pages).

(Continued)

*Primary Examiner* — Robert Long (57) ABSTRACT

A surgical instrument is designed for clamping, cutting, and/or joining tissue. This surgical instrument includes a handle portion, an elongate portion extending distally from the handle portion, first and second jaw members disposed adjacent a distal portion of the elongated portion, a shaft movable upon actuation of the handle portion, and a knife bar operatively coupled to the shaft. At least one of the jaw members is movable with respect to the other between an open position and an approximated position for engaging body tissue therebetween. The knife bar has a curved profile and moves along at least one of the jaw members upon movement of the shaft.

13 Claims, 9 Drawing Sheets

Related U.S. Application Data continuation of application No. 13/751,737, filed on Jan. 28, 2013, now Pat. No. 8,684,254, which is a continuation of application No. 12/707,770, filed on Feb. 18, 2010, now Pat. No. 8,393,516.

(60) Provisional application No. 61/155,635, filed on Feb. 26, 2009.

(51) Int. Cl.
*A61B 17/3209* (2006.01)
*A61B 17/072* (2006.01)
*A61B 17/068* (2006.01)
*A61B 17/29* (2006.01)
*A61B 17/32* (2006.01)

(52) U.S. Cl.
CPC .. *A61B 17/105* (2013.01); *A61B 2017/07221* (2013.01); *A61B 2017/2905* (2013.01); *A61B 2017/2923* (2013.01); *A61B 2017/320052* (2013.01)

(58) Field of Classification Search
CPC .......... A61B 2018/1455; A61B 1/0052; A61B 2017/061; A61B 2017/07221; A61B 2017/2945; A61B 2018/1432; A61B 2017/2926
USPC .................. 227/175.1–182.1; 606/1, 219
See application file for complete search history.

(56) References Cited

U.S. PATENT DOCUMENTS

| | | |
|---|---|---|
| 4,216,891 A | 8/1980 | Behlke |
| 4,354,628 A | 10/1982 | Green |
| 4,383,634 A | 5/1983 | Green |
| 4,506,671 A | 3/1985 | Green |
| 4,530,453 A | 7/1985 | Green |
| 4,566,620 A | 1/1986 | Green et al. |
| 4,568,009 A | 2/1986 | Green |
| 4,589,582 A | 5/1986 | Bilotti |
| 4,617,928 A | 10/1986 | Alfranca |
| 4,665,916 A | 5/1987 | Green |
| 4,684,051 A | 8/1987 | Akopov et al. |
| 4,715,520 A | 12/1987 | Roehr, Jr. et al. |
| 4,788,978 A | 12/1988 | Strekopytov et al. |
| 4,819,853 A | 4/1989 | Green |
| 4,869,414 A | 9/1989 | Green et al. |
| 4,881,545 A | 11/1989 | Isaacs et al. |
| 4,915,100 A | 4/1990 | Green |
| 5,046,250 A * | 9/1991 | Huang ...................... B25B 7/12 30/115 |
| 5,100,042 A | 3/1992 | Gravener et al. |
| 5,188,636 A | 2/1993 | Fedotov |
| 5,344,060 A | 9/1994 | Gravener et al. |
| 5,405,073 A | 4/1995 | Porter |
| 5,452,836 A | 9/1995 | Huitema et al. |
| 5,465,894 A | 11/1995 | Clark et al. |
| 5,547,117 A | 8/1996 | Hamblin et al. |
| 5,558,266 A | 9/1996 | Green et al. |
| 5,579,978 A | 12/1996 | Green et al. |
| 5,607,094 A | 3/1997 | Clark et al. |
| 5,632,746 A | 5/1997 | Middleman et al. |
| 5,706,997 A | 1/1998 | Green et al. |
| 5,706,998 A | 1/1998 | Plyley et al. |
| 6,805,273 B2 | 10/2004 | Bilotti et al. |
| 6,988,650 B2 | 1/2006 | Schwemberger et al. |
| 7,147,139 B2 | 12/2006 | Schwemberger et al. |
| 7,204,404 B2 | 4/2007 | Nguyen et al. |
| 7,207,472 B2 | 4/2007 | Wukusick et al. |
| 8,579,177 B2 * | 11/2013 | Beetel .................. A61B 17/068 227/175.1 |
| 8,641,598 B2 | 2/2014 | Green, II et al. |
| 8,899,462 B2 * | 12/2014 | Kostrzewski .... A61B 17/07207 227/175.1 |
| 8,925,787 B2 | 1/2015 | Kostrzewski |
| 2005/0139636 A1 | 6/2005 | Schwemberger et al. |
| 2005/0145672 A1 | 7/2005 | Schwemberger et al. |
| 2005/0247753 A1 | 11/2005 | Kelly et al. |
| 2006/0163312 A1 | 7/2006 | Viola et al. |
| 2006/0241692 A1 | 10/2006 | McGuckin et al. |
| 2007/0034668 A1 | 2/2007 | Holsten et al. |
| 2007/0039997 A1 | 2/2007 | Mather et al. |
| 2007/0114261 A1 | 5/2007 | Ortiz et al. |
| 2007/0187456 A1 | 8/2007 | Viola et al. |
| 2007/0225737 A1 | 9/2007 | Messerly et al. |
| 2008/0078800 A1 | 4/2008 | Hess et al. |
| 2008/0110958 A1 * | 5/2008 | McKenna ........ A61B 17/00491 227/176.1 |
| 2008/0110960 A1 | 5/2008 | Jankowski |
| 2008/0169332 A1 | 7/2008 | Shelton et al. |
| 2009/0005808 A1 | 1/2009 | Hess et al. |
| 2010/0213240 A1 * | 8/2010 | Kostrzewski ........ A61B 17/072 227/180.1 |

FOREIGN PATENT DOCUMENTS

| | | |
|---|---|---|
| GB | 2029754 A | 3/1980 |
| WO | 02/30296 A2 | 4/2002 |
| WO | 2006/055385 A2 | 5/2006 |

OTHER PUBLICATIONS

Canadian Office Action corresponding to counterpart Int'l Appln. No. CA 2,693,985.
Canadian Office Action corresponding to counterpart Int'l Appln. No. CA 2,693,985 dated Oct. 18, 2016.
European Office Action corresponding to counterpart Int'l Appln. No. EP 13 16 3500.5 dated Oct. 21, 2016.
European Search Report EP 09 25 1240 dated Oct. 5, 2009; (8 pages).
European Search Report EP 10 25 0334 dated Apr. 20, 2010; (8 pages).
European Search Report for EP 13163500.5-1659 date of completion is Oct. 23, 2013 (7 pages).
European Search Report for EP 13163501.3-1659 date of completion is Oct. 24, 2013 (6 pages).

* cited by examiner

SURGICAL STAPLING APPARATUS WITH CURVED CARTRIDGE AND ANVIL ASSEMBLIES

CROSS-REFERENCE TO RELATED APPLICATIONS

This application is a continuation of U.S. patent application Ser. No. 14/180,752 filed Feb. 14, 2014, now U.S. Pat. No. 8,925,787, which is a continuation of U.S. patent application Ser. No. 13/751,737 filed Jan. 28, 2013, now U.S. Pat. No. 8,684,254, which is a continuation of U.S. patent application Ser. No. 12/707,770 filed Feb. 18, 2010, now U.S. Pat. No. 8,393,516, which claims benefit of U.S. Provisional Application No. 61/155,635 filed Feb. 26, 2009, and the disclosures of each of the above-identified applications are hereby incorporated by reference in their entirety.

BACKGROUND

Technical Field

The present disclosure relates generally to a surgical instrument and, more specifically, to a surgical instrument for clamping, joining and/or cutting, and/or joining tissue.

Background of Related Art

Certain surgical stapling instruments are used for applying rows of staples through compressed living tissue. These surgical stapling instruments are employed, for example, for fastening tissue or organs prior to transection or resection or during anastomoses. In some cases, these surgical stapling instruments are utilized for occluding organs in thoracic and abdominal procedures.

Typically, such surgical stapling instruments include an anvil assembly, a cartridge assembly for supporting an array of surgical staples, an approximation mechanism for approximating the cartridge and anvil assemblies, an alignment or guide pin assembly for capturing tissue between the cartridge and anvil assemblies and for maintaining alignment between the cartridge and anvil assemblies during approximation and firing, and a firing mechanism for ejecting the surgical staples from the cartridge assembly.

In use, a surgeon initially advances the alignment pin assembly and subsequently approximates the anvil and cartridge assemblies. In some instruments, the alignment pin is automatically advanced with approximation of the anvil and cartridge assemblies. Next, the surgeon fires the instrument to place staples in tissue. Optionally, the surgeon may use the same instrument or a separate device to cut the tissue adjacent or between the row(s) of staples. In some instances, the stapler includes a knife which cuts tissue as the staples are fired.

In certain procedures, it may be difficult to access the target organ or tissue for resection and application of rows of staples. It would therefore be advantageous to provide a stapling instrument that improves access to hard to reach areas and provides improved maneuverability of the instrument.

SUMMARY

The present disclosure relates to a surgical instrument for joining and/or cutting tissue. The present disclosure provides in one aspect a surgical instrument comprising a handle portion, an elongate portion extending distally from the handle portion, and first and second jaw members disposed adjacent a distal portion of the elongated portion. At least one of the jaw members is movable with respect to the other jaw member between an open position and an approximated position for engaging body tissue therebetween. A shaft is adapted to rotate upon actuation of the handle portion. A knife bar is operatively coupled to the shaft. The knife bar has a curved profile and moves along at least one of the jaw members upon rotation of the shaft to cut tissue.

In one embodiment, the instrument further comprises a pinion rotatably mounted on a distal portion of the shaft and the knife bar includes a rack adapted to mesh with the pinion, the knife bar movable between a deployed position and a retracted position upon rotation of the pinion. In one embodiment, one of the jaw members includes a sleeve adapted to receive the knife bar when the knife bar is in the retracted position.

The instrument may further comprise a knife extending from the knife bar, wherein the knife moves along one of the jaw members when the knife bar moves in response to rotation of the shaft. A control switch can be provided to control a direction of movement of the knife bar.

In a preferred embodiment, the jaw members each have a curved profile. In a preferred embodiment, one of the jaw members contains a plurality of fasteners.

A tissue stop pin may be disposed on a distal portion of one of the jaw members, wherein the pin has a first position wherein it is out of engagement with one of the jaw members and a second position wherein it engages both jaw members.

In one embodiment, a clamp actuator is disposed on the handle portion, wherein the clamp actuator is operatively associated with at least one of the jaw members such that the jaw members are relatively movable between the open position and the approximated position upon actuation of the clamp actuator. A trigger is preferably disposed on the handle portion, wherein the shaft rotates upon actuation of the trigger.

In a preferred embodiment, the elongate portion has a curved section. In some embodiments, the shaft is flexible. In other embodiments, it is substantially rigid.

The present disclosure also provides in another aspect a surgical instrument comprising a handle portion and an elongate portion extending distally from the handle portion, wherein the elongate portion has a proximal section extending in a fixed first direction and a distal section extending in a fixed second different direction. A first jaw member is disposed adjacent the distal section of the elongated portion, has a substantially C-shaped configuration and contains a plurality of fasteners in at least one curved row. An opposing jaw member is disposed adjacent the distal section of the elongated portion and has a substantially C-shaped configuration, wherein at least one of the jaw members is movable between an open position and an approximated position for engaging body tissue therebetween.

In some embodiments, the elongated portion is flexible; in other embodiments it is substantially rigid.

In one embodiment, the instrument includes a shaft and a knife bar operatively coupled to the shaft, the knife bar having a curved profile, wherein the knife bar moves along at least one of the first and second jaw members between a retracted position and a deployed position upon rotation of the shaft. The instrument may further include a pinion rotatably mounted on a distal end of the shaft, wherein the knife bar includes a rack adapted to mesh with the pinion.

The instrument may include a knife bar and a knife extending from the knife bar, wherein the first jaw member and the second jaw member each includes a knife channel for guiding movement of the knife along the first and second jaw members. The first jaw member may include a sleeve adapted to receive the knife bar.

In another aspect, the present disclosure provides a surgical instrument comprising a handle portion, an elongate portion extending distally from the handle portion and having a curved section, and first and second curved jaw members disposed adjacent a distal portion of the elongated portion. The first jaw member is movable with respect to the second jaw member in a substantially parallel closure movement between an open position and an approximated position for engaging body tissue therebetween. One of the jaw members has a plurality of fasteners contained therein arranged in an arcuate row.

In one embodiment, the instrument includes a slidable clamp arm for moving the first jaw member in the substantially parallel closure movement, wherein the clamp arm moves in a direction substantially parallel to a direction of movement of the fasteners when fired.

The surgical instrument may further include a tissue stop pin extending from one of the jaw members and movable into engagement with the other jaw member when the first jaw member is moved to the approximated position.

BRIEF DESCRIPTION OF THE DRAWINGS

Various embodiments of the presently disclosed surgical instrument are disclosed herein with reference to the drawings, wherein.

DETAILED DESCRIPTION OF THE EMBODIMENTS

Embodiments of the presently disclosed surgical instrument are described in detail with reference to the drawings, wherein like reference numerals designate corresponding elements in each of the several views. In the description that follows, the term "proximal" refers to the end or portion of the surgical instrument closer to the user, whereas the term "distal" refers to the end or portion of the surgical instrument further from the user.

In the interest of brevity, the present disclosure focuses on end effectors for the disclosed surgical instrument. U.S. Patent Application 2007/0187456, filed on Apr. 10, 2007, the entire contents of which are hereby incorporated by reference, describes in detail the structure and operation of an actuator and handle assembly which can be utilized in an embodiment of surgical instrument 100.

Figure 1:
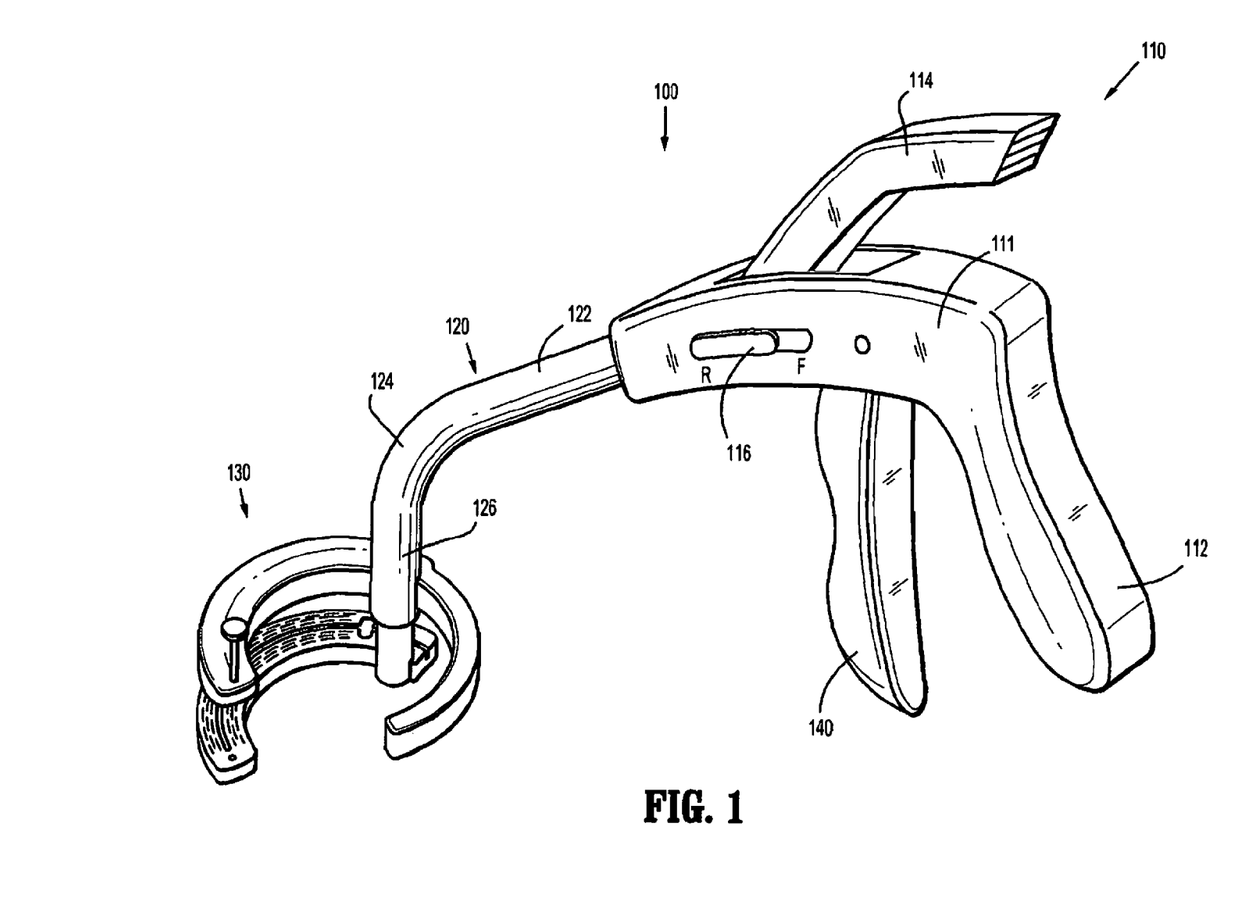
FIG. 1 is a perspective view of a surgical instrument according to an embodiment of the present disclosure with the end effector in an open position.

FIG. 1 illustrates an embodiment of a surgical instrument 100 designed for clamping, cutting, and/or joining tissue. Surgical instrument 100 generally includes a handle portion 110 having a handle housing 111, an elongate portion or shaft 120, and an end effector 130. Elongate portion 120 extends distally from handle portion 110 and has a proximal straight section 122, an elbow or curved section 124, and a distal straight section 126. In one embodiment, proximal straight section 122 is oriented substantially perpendicular relative to the distal straight section 126. However, other angles are also contemplated. Also, instead of straight sections, the elongated portion can be curved or have a series of different curves. In the illustrated embodiment, the elongated portion is substantially rigid so the configuration of the elongated portion does not change. In other embodiments, the elongated portion can be flexible so it can be changed to different configurations and angles.

With continued reference to FIG. 1, end effector 130 is coupled to distal straight section 126 of elongate portion 120 and handle portion 110 is connected to proximal straight section 122 of elongate portion 120. As noted above, it is also contemplated that the elongated portion 120 can have curved section(s) instead of the straight sections as long as the end effector 130 is angled with respect to the instrument.

Figure 2:
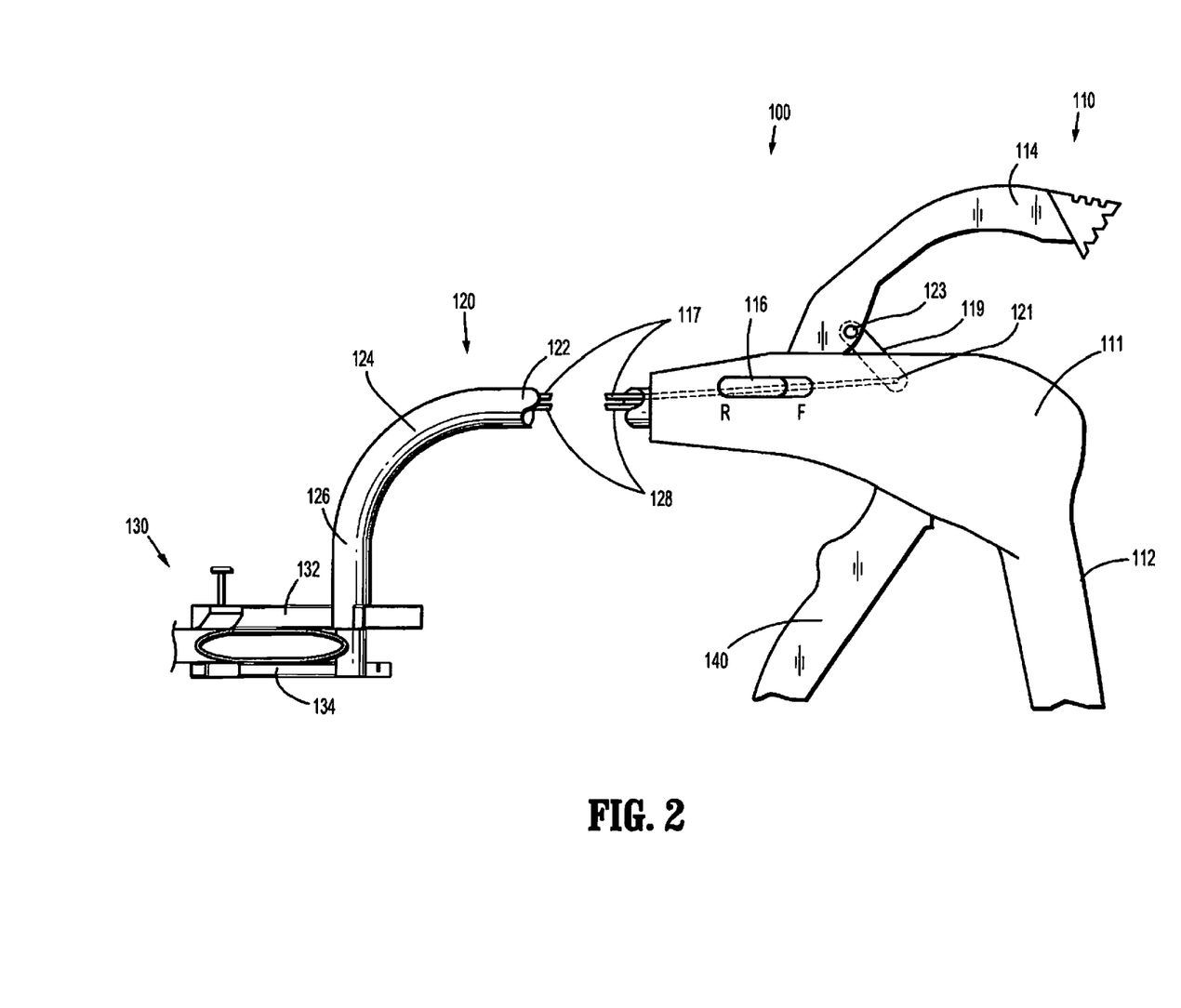
FIG. 2 is a side cross-sectional view of the surgical instrument shown in FIG. 1 with the end effector in an open position.
Figure 3:
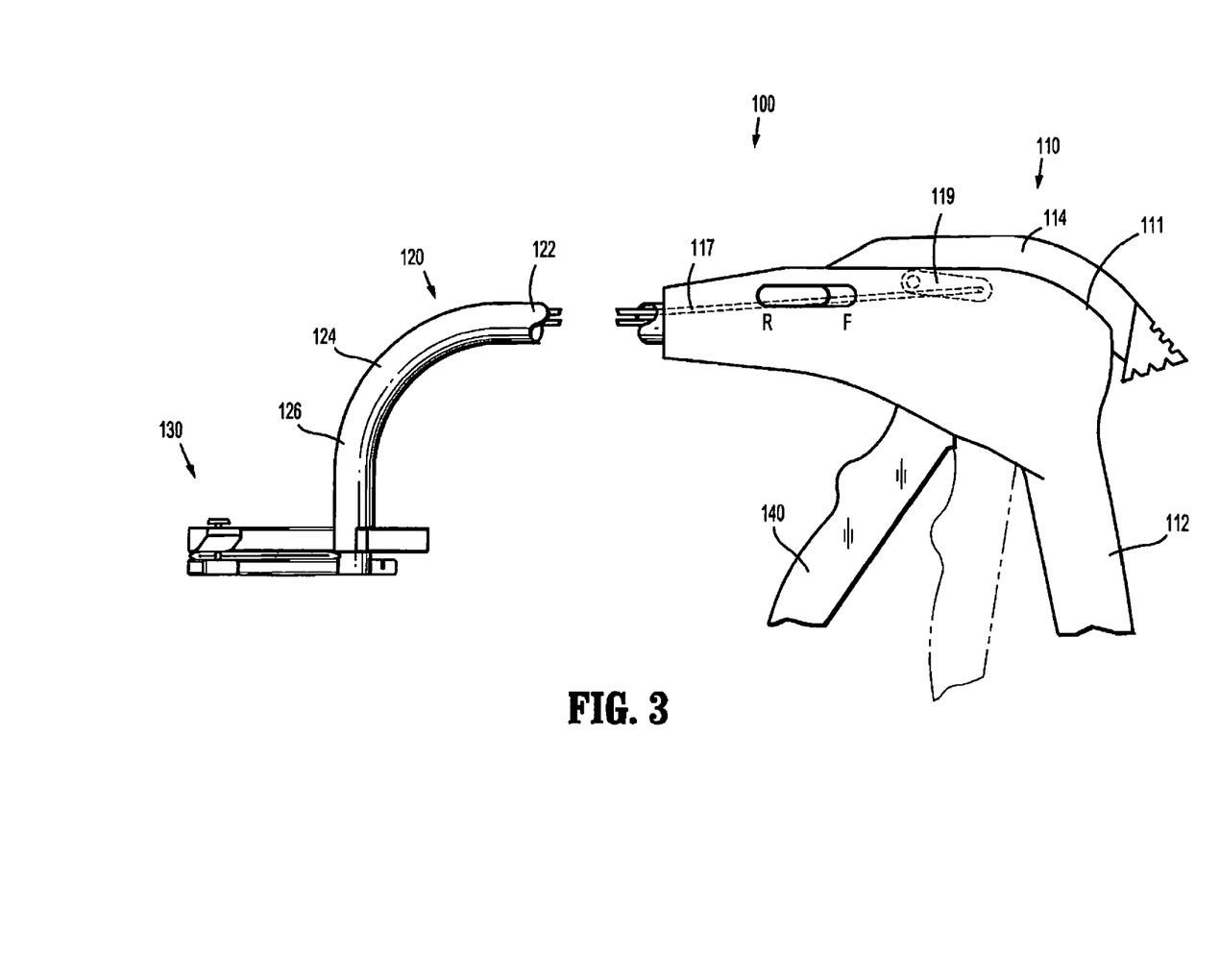
FIG. 3 is a side cross-sectional view of the surgical instrument of FIG. 1 with the end effector in an approximated position.

As seen in FIGS. 1-3, handle portion 110 contains a stationary handle 112, a clamp actuator 114 for moving end effector 130 between an open position and an approximated position, and a trigger 140 for firing fasteners 170 (FIG. 6) and/or displacing knife 144 (FIG. 4) along end effector 130 between a retracted position and a deployed (advanced) position. As shown in the orientation of the instrument of FIG. 1, handle 112 and trigger 140 extend downwardly with respect to the instrument 10 such that they are transverse to a longitudinal axis extending through the housing 115. Thus, the handle 112 and trigger 140 are positioned on one side of the instrument 10. In the illustrated embodiment, due to the curve of the elongated portion 120, the end effector 130 is also positioned on the same first side of the instrument.

Clamp actuator 114 is configured to move relative to handle portion 110 and is operatively coupled to the end effector 130. Clamp actuator 114 is shown in the embodiment of FIG. 1 as extending from an opposing side of the housing 115 from which the handle 112 and trigger 140 extend. In operation, the actuation of clamp actuator 114 by moving actuator 114 toward the handle housing 111 causes end effector 130 to move between the open position (FIG. 2) and the approximated position (FIG. 3). As shown, in the open position of FIG. 2, first and second jaw members 134, 132 are spaced further apart and in the approximated or closed position of FIG. 3, jaw members 134, 132 are closer together as jaw member 134 moves toward jaw member 132.

In the embodiment depicted in FIG. 1, clamp actuator 114 is a lever pivotably mounted within the handle body 111, but it is envisioned that clamp actuator 114 may be a switch, a button, a knob, a toggle, or any other suitable device or mechanism to approximate the end effector. Trigger 140 is movable relative to stationary handle 112 and is operatively associated with end effector 130. In use, trigger 140 is actuated by movement toward stationary handle 112 (shown in phantom in FIG. 3) to fire fasteners 170 (FIG. 6) and/or displace knife 144 (FIG. 4) along end effector 130 between a retracted position and a deployed (advanced) position.

Figure 4:
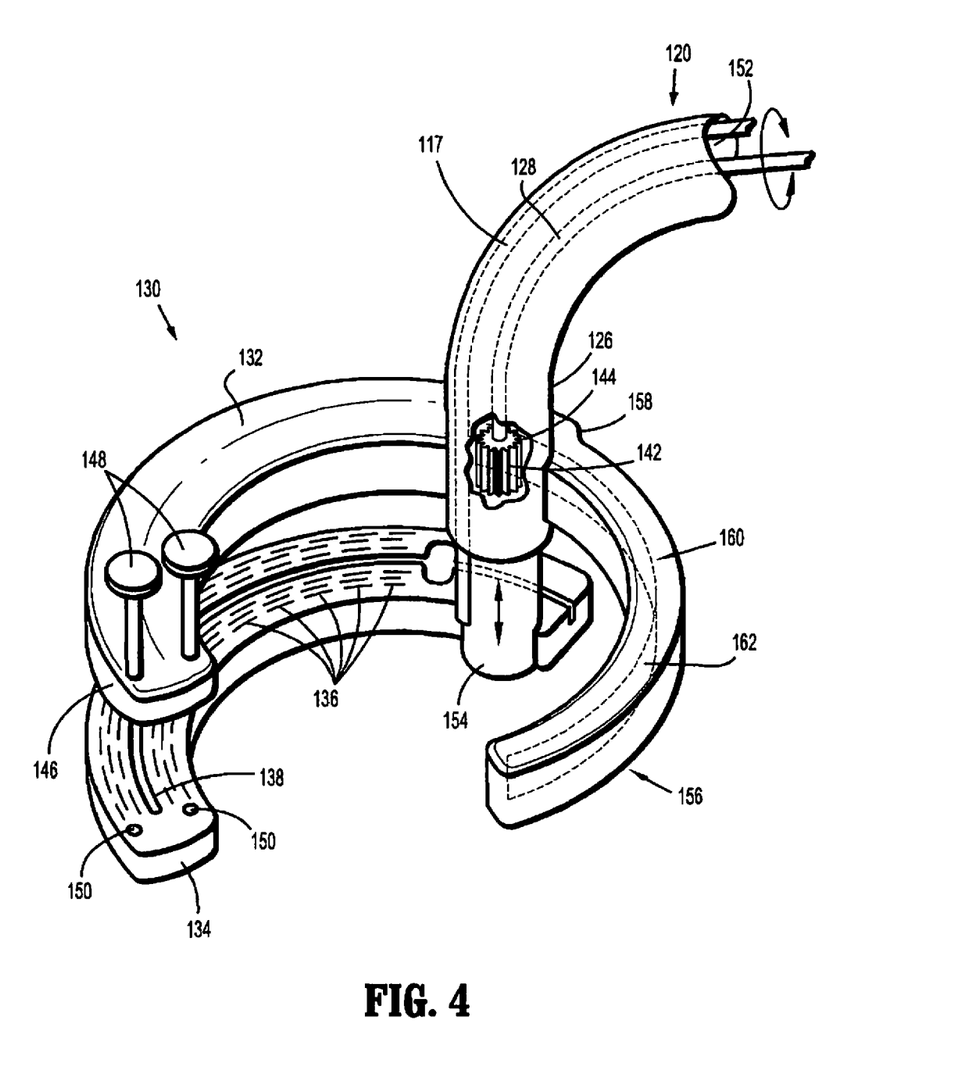
FIG. 4 is a close up perspective view of the end effector and a section of an elongate portion of the surgical instrument shown in FIG. 1.
Figure 5:
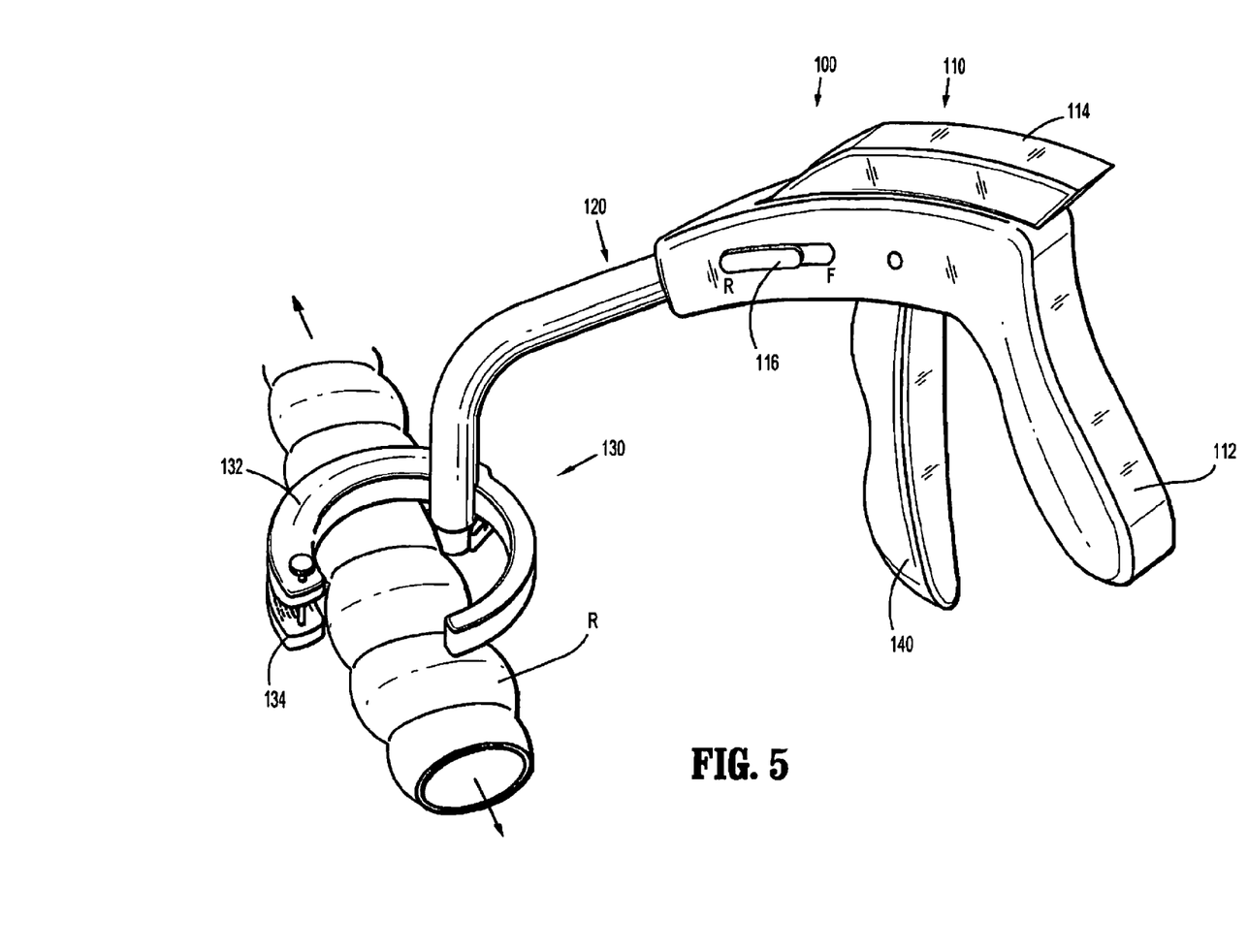
FIG. 5 is a perspective view of the surgical instrument shown in FIG. 1 with the end effector engaging body tissue.

Handle portion 110 further includes a control switch 116 on handle body 111 adapted to control the direction of the movement of knife bar 162 (FIGS. 4 and 5). Control switch 116 is movable between a first position, e.g. a forward position, and a second position, e.g. a reverse position. Preferably, indicia on the handle body, e.g. of "R" and "F" will indicate to the user the position of the switch 116. When control switch 116 is in the forward position, actuation of trigger 140 causes knife bar 162 (FIG. 4) to advance distally along end effector 130. Conversely, knife bar 162 (FIG. 4) moves proximally along end effector 130 upon actuation of trigger 140 when control switch 116 is in the reverse position. In one embodiment, control switch 116 is electromechanically coupled to a motor (not shown) and controls the direction of the motor rotation. In this embodiment, the motor is operatively coupled to a shaft 128 at least partially disposed inside elongate portion 120.

With reference to FIG. 4, surgical instrument 100 includes shaft 128 configured to rotate upon actuation of trigger 140 (FIG. 1). Shaft 128 extends through elongate portion 120 and is operatively connected to trigger 140. In one embodiment, shaft 128 is made of a flexible material. A gear mechanism, a motor, or any other suitable device or mechanism, may operatively interconnect trigger 140 (FIG. 1) and shaft 128. In one embodiment, trigger 140 is operatively associated with a motor (not shown) and shaft 128 is connected to the motor, such that actuation of trigger 140 activates the motor and, in turn, shaft 128 rotates upon activation of the motor. The motor may be positioned inside handle portion 110 or outside of surgical instrument 100. A pinion 142 is connected to a distal end of shaft 128 and is disposed in mechanical cooperation with end effector 130.

With continued reference to FIG. 4, end effector 130 includes first and second jaw members 134, 132 configured to collectively clamp tissue. The jaw members 132, 134 are preferably substantially C-shaped as shown, preferably extending in an arc greater than ninety degrees and preferably in an arc of between about 120 and about 180 degrees, although other arcs are contemplated. First and second jaw members 134, 132 are adapted to move between an open position (FIG. 2) and an approximated (closed) position (FIG. 3) upon actuation of clamp actuator 114. During operation, tissue or an organ is placed between first and second jaw members 134, 132, as illustrated in FIG. 2, and then clamp actuator 114 is actuated as shown in FIG. 3 to clamp the tissue positioned between the first and second jaw members 134, 132. In the embodiment shown in FIG. 4, first jaw member 134 corresponds to an anvil having an anvil surface with pockets to form the fasteners, while second jaw member 132 corresponds to a cartridge jaw containing the fasteners. The jaw member 134 preferably moves in a substantially parallel closure fashion as described in more detail below. Although described herein as anvil jaw 134 moving with respect to stationary cartridge jaw 132, it is also contemplated that cartridge jaw 132 is movable while the anvil jaw 134 remains stationary, or that both jaws 132, 134 are movable. Thus, relative movement means either one of the jaws or both of the jaws are movable.

Distal section 126 of elongate portion 120 is connected to first jaw member 134. Elongate portion 120 defines a bore 152 extending therethrough. Bore 152 is configured to slidably receive a tubular member or guide 154 attached to second jaw member 134. Tubular member 154 is adapted to move through a portion of bore 152 upon actuation of clamp actuator 114 as it is operatively connected to the actuator 114 by closure rod 117. More specifically, closure rod 117 is connected to one end of link 119 (via pin 121) which is connected at an opposing end to actuator 114 via pin 123 (see FIG. 2). When a user actuates clamp actuator 114, tubular member 154 moves further inside bore 152 of elongate portion 120 as it is pulled back by jaw closure rod 117 due to pivoting of link 119 and consequently pulls second jaw member 132 toward first jaw member 134 to move end effector 130 to the approximated position (FIG. 3). As end effector 130 moves to the approximated position, surgical instrument 100 clamps the tissue situated between first and second jaw members 134, 132. As can be appreciated by comparing FIGS. 2 and 3, jaw 134 slides upwardly (in the orientation of the Figures) toward jaw 132, the jaws remaining substantially parallel during the closure movement.

Second jaw member 132 has a curved profile and is oriented substantially parallel to first jaw member 134. In addition, jaw member 132 includes at least one stop pin 148 disposed at a distal end 146 thereof. In the embodiment shown in FIG. 4, jaw member 132 includes two stop pins 148. Each stop pin 148 is configured to engage second jaw member 134 when in an approximated position. In the open position, each stop pin 148 is spaced apart from jaw member 134 and, in the approximated position, each stop pin 148 engages a respective opening 150 formed on second jaw member 134. When stop pins 148 are in the approximated position, stop pins 148 prevent or inhibit tissue from escaping end effector 130 while the tissue is being clamped between first and second jaw members 134, 132.

In one embodiment, jaw member 132 includes a curved knife channel (not shown) between the two sets of annular rows of fasteners which are adapted to slidably receive curved knife bar 162. Jaw member 132 preferably includes a plurality of fasteners contained therein arranged in two sets of three arcuate rows and a plurality of corresponding slots through which the fasteners are ejected. A different number of fastener rows (and slots) is also contemplated.

First jaw member 134 also has a curved profile mirroring the curved profile of second jaw member 132. Second jaw member 134 includes rows of fastener forming or anvil pockets 136 (shown schematically) corresponding to the rows of fasteners and extending along the curved profile of jaw member 134. In the embodiment shown in FIG. 4, jaw member 134 includes two sets of three arcuate rows of pockets 136 corresponding to the fasteners of second member 132. An arcuate knife channel 138 is located between the two sets of three rows of slots 136 and adapted to slidably receive knife bar 162. First jaw member 134 and first jaw member 132 may alternatively include more or fewer rows of slots/staple forming pockets. Each anvil pocket 136 is configured to receive a fastener 170 (FIG. 6) to deform the fastener. Fastener 170 may be a staple or any other suitable fastener. Rows of pockets 136 as well as knife channel 138 extend along the curved profile of first jaw member 134.

Figure 4A:
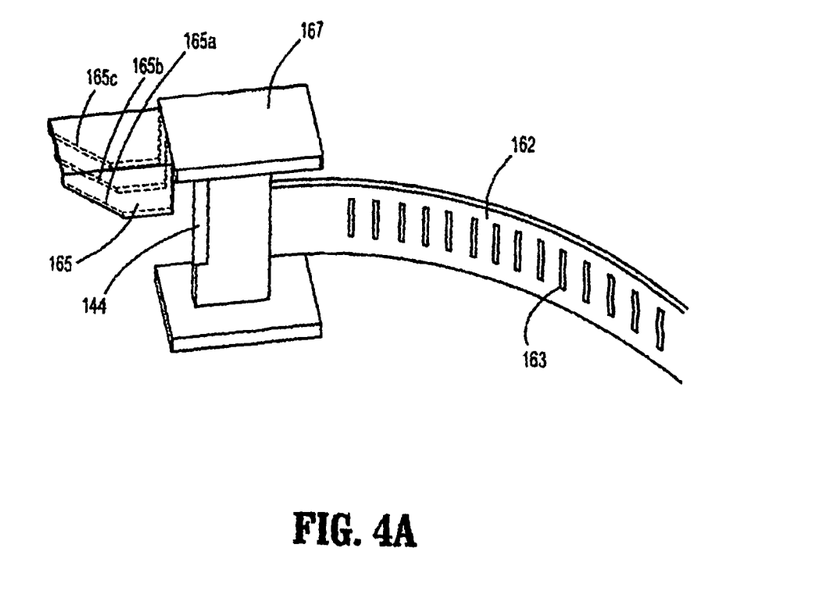
FIG. 4A is a close up perspective view of a portion of the knife bar and camming member of the end effector.

Jaw member 132 includes a sleeve 156 extending from end 158 thereof. Sleeve 156 has a curved profile and is configured to receive knife assembly 160. Sleeve 156 could be integral with jaw member 132 or a separate component attached thereto. Knife assembly 160, a portion of which is shown in FIG. 4A, includes a knife bar 162 and a knife or blade 144 extending from an end of knife bar 162. The knife can be integral with the knife bar 162 or alternatively a separate component attached to the knife bar 162. Knife bar 162 has a curved profile mirroring the curved profile of knife channel 138 and includes a rack 163 adapted to mesh with pinion 142. In operation, as shaft 128 rotates, pinion 142 rotates and meshes with the rack 163 of knife bar 162 to displace knife bar 162 along knife channel 138 (and the channel in jaw member 132) from the retracted position within sleeve 156 to the deployed position in a stepped incremental movement. While knife bar 162 moves along the knife channel, knife 144 cuts the tissue clamped between first and second jaw members 132, 134.

In one embodiment, knife bar 162 is operatively attached to an actuation sled 165 disposed within first jaw member 132. The actuation sled is configured to move through first jaw member 132 and engage staple pushers (not shown) disposed in the fastener slots (not shown). For clarity, only one actuation sled 165 is shown in FIG. 4A. If two sets of three rows of staples are provided, another sled 165 would be provided. When the camming surfaces 165a, 165b and 165c of actuation sled engage the staple pushers, fasteners 170 disposed in the slots are ejected from first jaw member 132 in a direction transverse to the direction of movement of the sled and forced through the tissue and into engagement with staple forming pockets 136 to form the fasteners. That is, in operation, actuation sled moves through the second jaw member 132 as knife bar 162 moves along end effector 130 between the retracted position and the deployed position, with knife slot 138 of jaw member 134 and the knife slot of jaw member 132 accommodating the knife 144. (The knife bar 162 or knife can optionally be attached to the actuation sled). While the actuation sled moves through the second jaw member 132, the actuation sled moves the staple pushers toward first jaw member 134. As the staple pushers move toward second jaw member 132, fasteners 170 are ejected from second jaw member 132 and forced through tissue and into engagement with the anvil pockets for formation of the fasteners. The knife bar 162 includes an I-beam structure 167 which rides in the respective jaws 134, 132 to help maintain the gap between jaws 134, 132.

Figure 6:
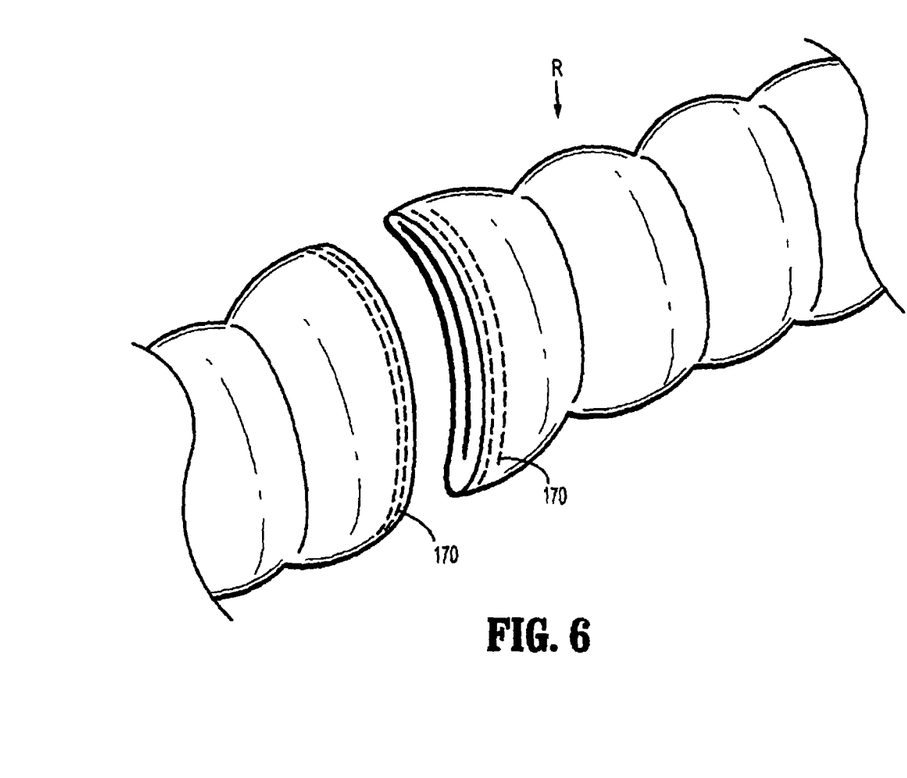
FIG. 6 is a perspective view of the body tissue depicted in FIG. 5 after it has been cut and surgically joined by the surgical instrument shown in FIG. 1.

With reference to FIGS. 5 and 6, physicians may employ surgical instrument 100 for a wide range of surgical procedures. For instance, physicians may use surgical instrument 100 in a lower anterior resection (LAR). In such procedures, the curved profiles of first and second jaw members 134, 132 and the particular shape of elongate portion 120 allows the physician to operate in hard-to-reach organs such as the rectum, which is located deep in a patient's pelvis.

In one exemplary surgical procedure, the physician initially places first and second jaw members 134, 132 in the open position, as shown in FIG. 2. The physician then moves end effector 130 to the target tissue or organ, such as rectum "R," and places at least a portion of the target tissue or organ between first and second jaw members 132, 134, as illustrated in FIG. 5. Subsequently, the physician actuates clamp actuator 114, as shown in FIG. 3, to move first and second jaw members 134, 132 to the approximated position, thereby clamping the target tissue between first and second jaw members 134, 132.

After clamping the target tissue, the physician moves control switch 116 to the forward position to set the knife bar to the advancement position. Then, the physician squeezes trigger 140, as shown in phantom in FIG. 3 (the trigger motion transferred into rotary motion of the drive shaft which is transferred by the rack and pinion to linear motion of the sled and/or knife bar), to fire fasteners 170 (FIG. 6) housed in second jaw member 132 and advances knife bar 162 (FIG. 4) along end effector 130 from a retracted position to a deployed position. In one embodiment, the trigger is squeezed to advance the actuator sled and knife bar its full distance through the jaw members 132, 134. In other embodiments, a clutch mechanism can be provided so that the multiple squeezes of the trigger are required for full firing. In this embodiment, the user can decide the length of the resection arc.

FIGS. 5A-5D illustrate an example, shown schematically, of a gear mechanism which provides incremental (stepped) movement the knife bar 162. That is, each squeeze of the trigger 140 increasingly moves the knife bar 162 by rotating the gear.

Trigger 140 pivots about pivot pin 146 and is biased to a forward position by reset spring 147. Attached to trigger 140 is ratchet pawl 180 engagable with drive rack 182 positioned in the handle housing of the instrument 100. Drive rack 182 has upper teeth 184 engagable with stationary drive gear 186. Consequently, when trigger 140 is pulled proximally, drive rack 182 is advanced distally in the direction of the arrow of FIG. 5D due to the engagement of ratchet pawl 180 with lower teeth 183 of drive rack 186. Distal movement of drive rack 182 causes rotation of drive gear in a first direction, e.g. clockwise as shown in the orientation of FIG. 5D. A reset pawl 190 positioned in the handle housing interlocks with lower teeth 183 of rack 182 to hold the rack 182 and the knife bar in a distal position.

Figure 5A:
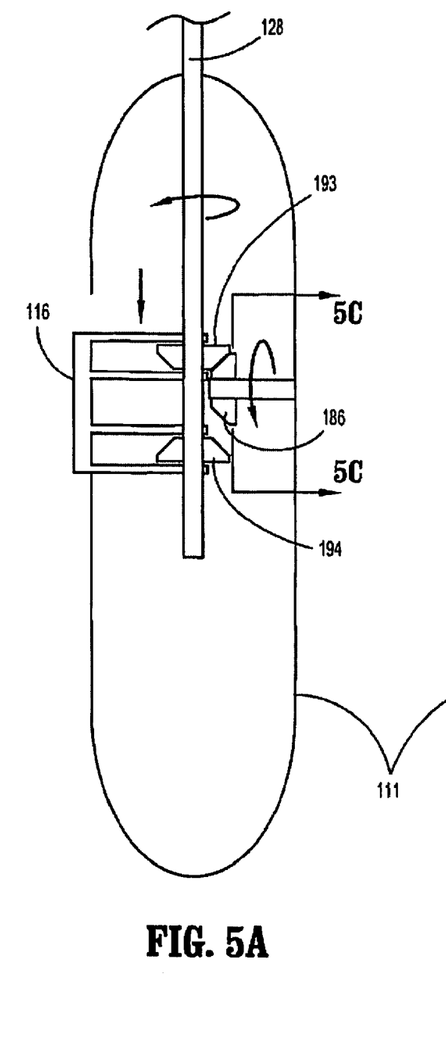
FIGS. 5A and 5B are schematic views of the gear mechanism for driving the knife bar in the forward and reverse directions, respectively.
Figure 5B:
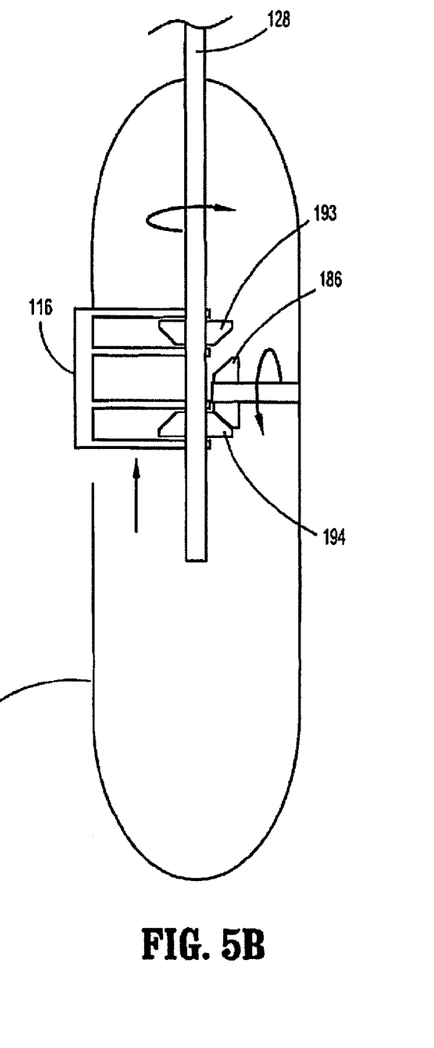
Figure 5C:
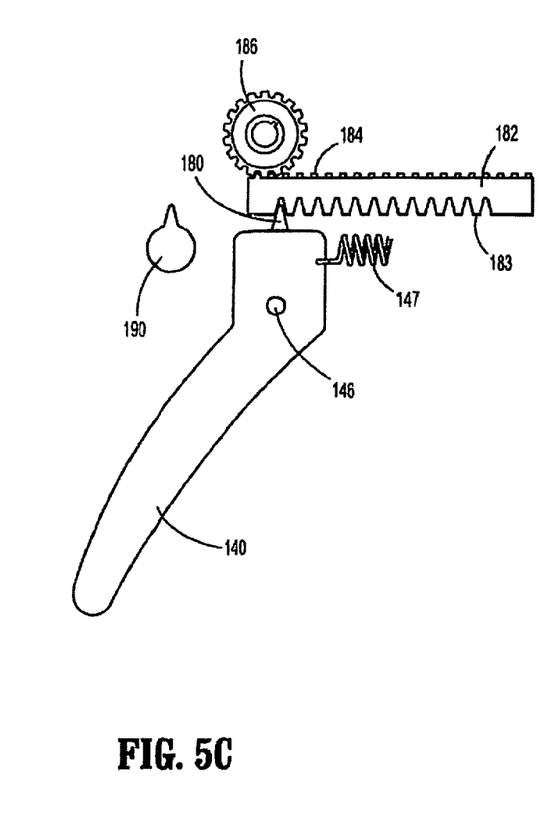
FIGS. 5C, 5D and 5E are schematic views illustrating movement of the trigger to rotate the drive gear to advance the knife bar.
Figure 5D:
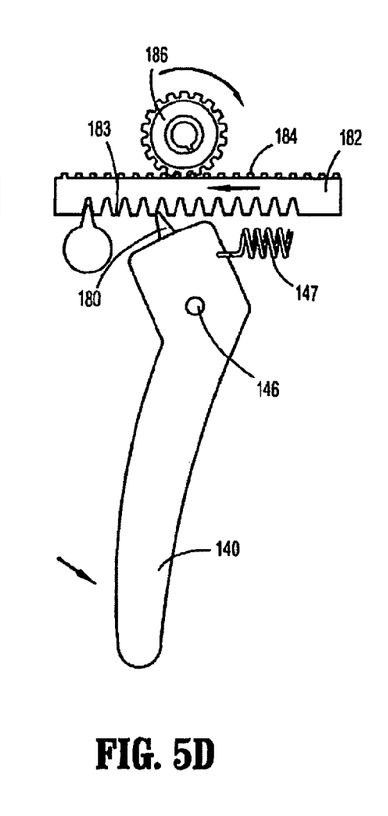
Figure 5E:
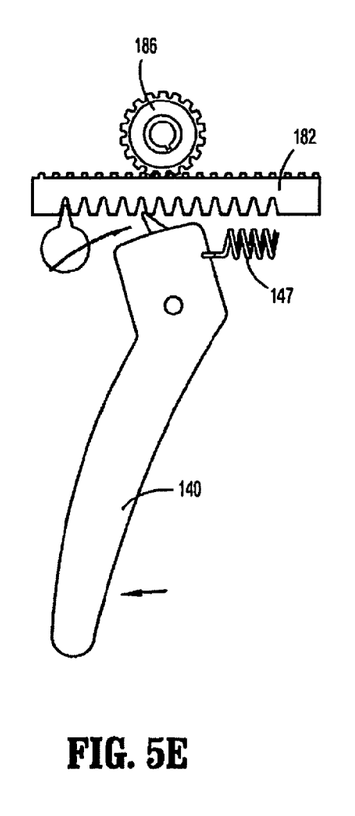

An example of a switching mechanism is shown schematically in FIGS. 5A and 5B. In a first position of the switch, slidable bevel gear 193 engages stationary drive gear 186. Consequently, when drive gear 186 is rotated as described above, drive shaft 128 will rotate in a first direction, indicated as counterclockwise in the orientation of FIG. 5A. This advances the knife bar 162 to fire the fasteners. For reverse movement of the knife bar 162 after firing of the fasteners, the switch 116 is slid to a second position to disengage first bevel gear 192 from engagement with drive gear 186 and to move second bevel gear 193 into engagement with drive gear 186. Consequently, when drive gear 186 is rotated in the manner described above, drive rod 128 will rotate in the opposite direction, e.g. clockwise as viewed in the orientation of FIG. 5B, thereby moving the knife bar 162 in the reverse direction to retract the sled and fasteners from the channel.

Upon firing of surgical instrument 100, knife 144 cuts the clamped tissue and fasteners 170 (FIG. 6) join or seal portions of the clamped tissue. In the case of LAR, surgical instrument 100 effectively divides rectum "R" in two portions and seals the two resulting portions with fasteners 170 ejected from end effector 130, as seen in FIG. 6. To remove surgical instrument 100 from the operating site, the physician moves the switch to the reverse position, releases trigger 140 to move it back to its original position thereby retracting the sled and knife bar 162 from its advanced (deployed) position within jaw 132 to its retracted position within extension sleeve 156. (In some embodiments, multiple squeezes may be required to retract the knife bar.) The user then moves first and second jaw members 134, 132 to the open position by moving the clamp lever 114 back to its original position, thereby advancing sleeve 154 distally to thereby move anvil jaw 134 away from cartridge jaw 132 to release the target tissue. Instrument 100 can then be withdrawn from the patient's body.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

What is claimed is:

1. A surgical instrument, comprising:
   a first jaw member;
   a second jaw member, wherein at least one of the jaw members is movable relative to the other jaw member between an open position and an approximated position;
   a shaft disposed in mechanical cooperation with at least one of the jaw members;
   a pinion disposed adjacent a portion of the shaft, wherein the pinion is rotatably mounted on a distal end of the shaft; and
   a knife bar including a rack adapted to mesh with the pinion, the knife bar movable with respect to at least one of the jaw members between a retracted position and a deployed position upon rotation of the shaft.

2. The surgical instrument of claim 1, wherein each of the jaw members includes a curved configuration.

3. The surgical instrument of claim 2, wherein the knife bar includes a curved profile.

4. A surgical instrument, comprising:
   a first jaw member;
   a second jaw member, wherein at least one of the jaw members is movable relative to the other jaw member between an open position and an approximated position;
   a shaft disposed in mechanical cooperation with at least one of the jaw members;
   a pinion disposed adjacent a portion of the shaft;
   a knife bar including a rack adapted to mesh with the pinion, the knife bar movable with respect to at least one of the jaw members between a retracted position and a deployed position upon rotation of the shaft; and
   a knife extending from the knife bar, wherein at least one of the jaw members includes a sleeve adapted to receive the knife bar in a retracted position, and wherein the knife bar is movable in a continuous path between the sleeve and the at least one jaw member.

5. The surgical instrument of claim 4, wherein each of the jaw members includes a knife channel for guiding movement of the knife along the first jaw member and the second jaw member.

6. The surgical instrument of claim 4, wherein the sleeve is configured to receive at least a majority of the knife bar in a retracted position.

7. The surgical instrument of claim 4, wherein the sleeve is included on only one of the first jaw member or the second jaw member.

8. An end effector for use with a surgical instrument, the end effector comprising:
   a first jaw member;
   a second jaw member, wherein at least one of the first jaw member or the second jaw member is linearly movable in a first direction between an open position and an approximated position with respect to the other jaw member; and
   a cutting member movable in a second direction with respect to the first jaw member, the first direction being non-parallel to the second direction, wherein the first jaw member includes a sleeve adapted to receive the cutting member in a retracted position.

9. The end effector of claim 8, wherein the cutting member includes a knife extending therefrom, and wherein each of the first jaw member and the second jaw member includes a knife channel for guiding movement of the knife along the first jaw member and the second jaw member.

10. The end effector of claim 8, wherein the sleeve is configured to receive at least a majority of the cutting member in a retracted position.

11. The end effector of claim 8, wherein the sleeve is included on only one of the first jaw member or the second jaw member.

12. The end effector of claim 8, wherein each of the first jaw member and the second jaw member includes a curved configuration.

13. The end effector of claim 8, wherein the cutting member includes a rack adapted to mesh with a pinion of the surgical instrument.

* * * * *